(12) United States Patent
Steinmueller (10) Patent No.: US 9,615,738 B2
(45) Date of Patent: Apr. 11, 2017

(54) METHOD AND ANALYSIS APPARATUS FOR MEASURING A CORNEA

(71) Applicant: Oculus Optikgeraete GmbH, Wetzlar (DE)

(72) Inventor: Andreas Steinmueller, Wettenberg (DE)

(73) Assignee: OCULUS OPTIKGERAETE GMBH, Wetzlar (DE)

( * ) Notice: Subject to any disclaimer, the term of this patent is extended or adjusted under 35 U.S.C. 154(b) by 247 days.

(21) Appl. No.: 13/903,423

(22) Filed: May 28, 2013

(65) Prior Publication Data

US 2013/0329187 A1   Dec. 12, 2013

(30) Foreign Application Priority Data

Jun. 8, 2012  (DE) .................. 10 2012 209 667

(51) Int. Cl.
    *A61B 3/107*   (2006.01)
(52) U.S. Cl.
    CPC .................... *A61B 3/107* (2013.01)
(58) Field of Classification Search
    CPC ......... A61B 3/14; A61B 3/0025; A61B 3/102; A61B 3/12; A61B 3/0008; A61B 3/113; A61B 3/1005; A61B 3/107; A61B 3/0091; A61B 3/0033; A61B 3/1015; A61B 3/1025; A61B 3/103; A61B 3/18; A61B 3/0058; A61B 3/0075; A61B 3/10; A61B 3/11
    USPC ....... 351/205, 210, 211, 212, 221, 246, 247, 351/206; 600/401, 405; 356/601, 610; 702/42, 50
    See application file for complete search history.

(56) References Cited

U.S. PATENT DOCUMENTS

| | | | |
|---|---|---|---|
| 5,116,115 A | 5/1992 | Lange et al. | |
| 5,936,706 A | 8/1999 | Takagi | |
| 2006/0028619 A1 | 2/2006 | Fujieda et al. | |
| 2006/0109423 A1* | 5/2006 | Wang | A61B 3/101 351/206 |
| 2006/0187413 A1* | 8/2006 | Applegate et al. | 351/246 |
| 2006/0241367 A1* | 10/2006 | Koest | A61B 3/165 600/405 |
| 2007/0273611 A1* | 11/2007 | Torch | A61B 3/0066 345/8 |

(Continued)

FOREIGN PATENT DOCUMENTS

| | | |
|---|---|---|
| JP | 2004113380 A | 4/2004 |
| JP | 2010057897 A | 3/2010 |

OTHER PUBLICATIONS

Mas, et al., Custom Designed Dynamic Videokeratometer, Journal of Modern Optics, 2010, 57(2):94-102.*

(Continued)

*Primary Examiner* — Scott J Sugarman
*Assistant Examiner* — Sharrief Broome
(74) *Attorney, Agent, or Firm* — Quarles & Brady LLP (57) ABSTRACT

A method and an analysis apparatus for measuring a cornea of an eye includes an ophthalmological analysis system. The ophthalmological analysis system measures a topography of a cornea in a measurement time interval to obtain a number of image data sets of a surface area of the cornea experiencing a change in intraocular pressure. A repeated change in the topography of the cornea is determined from the number of image data sets.

18 Claims, 4 Drawing Sheets

(56) References Cited

U.S. PATENT DOCUMENTS

2010/0238408 A1* 9/2010 Roberts .................. A61B 3/165
  351/212

OTHER PUBLICATIONS

Kowalska, et al., Comparison of High-Speed Videokeratoscopy and Ultrasound Distance Sensing for Measuring the Longitudinal Corneal Apex Movements, Ophthalmic and Physiological Optics, 2009, 29:227-234.*

Alonso-Caneiro, et al., Estimating Corneal Surface Topography in Videokeratoscopy in the Presence of Strong Signal Interference, IEEE Transactions on Biomedical Engineering, 2008, 55(10):2381-2387.

Danielewska, et al., Phase Dependencies Between Longitudinal Corneal Apex Displacement of Human Eye and Cardiovascular System, Proc. of SPIE, 2008, vol. 7141, pp. 714117-1-714117-6.

Kowalska, et al., Ultrasonic Measurement of Binocular Longitudinal Corneal Apex Movements and Their Correlation to Cardiopulmonary System, Biocybernetics and Biomedical Engineering, 2008, 28(3):35-43.

Kowalska, et al., Ultrasonic In-Vivo Measurement of Ocular Surface Expansion, IEEE Transactions on Biomedical Engineering, 2011, 58(3):674-680.

The State Intellectual Property Office of P. R. China, First Office Action and Search Report, Application No. 201310221600.6, Dec. 2, 2014, 15 pages [English Language Translation Only].

Korean Intellectual Property Office, Notice of Rejection, Application No. 10-2013-0063526, Aug. 16, 2016 [English Language Translation Only].

* cited by examiner

METHOD AND ANALYSIS APPARATUS FOR MEASURING A CORNEA

CROSS REFERENCE TO RELATED APPLICATION

The present application claims the benefit of German Patent Application No. 10 2012 209 667.1 filed Jun. 8, 2012, which is fully incorporated herein by reference.

STATEMENT REGARDING FEDERALLY SPONSORED RESEARCH OR DEVELOPMENT

Not applicable.

FIELD OF THE INVENTION

The invention relates to a method and an ophthalmological analysis apparatus for measuring a cornea of an eye to be examined, in particular of a person, with an ophthalmological analysis system, wherein, with the ophthalmological analysis system, a topography of a cornea is measured, wherein, with the ophthalmological analysis system, in a measurement time interval, a number of image data sets of a surface area of the cornea is obtained, wherein, in the measurement time interval, a change in an intraocular pressure of an eye is effected by a cardiovascular activity, wherein, due to said change in the intraocular pressure, a repeated change in the topography of the cornea in the measurement time interval is caused.

BACKGROUND OF THE INVENTION

Ophthalmological analysis systems for measuring a topography of a cornea are sufficiently known and are used in different versions, for instance for measuring the cornea or for determining astigmatism. Furthermore, central and peripheral radii of curvature of the cornea can be measured, which can subsequently be utilized for fitting a contact lens. Here, so-called keratometric analysis apparatuses also serve, amongst other things, to determine a keratoconus and to calculate an intraocular lens. By means of a measurement of a topography of the cornea, it becomes possible to describe a surface progression of a corneal surface, and thus, for instance, to determine a keratoconus. In particular with a keratoconus, there is the problem that it can only be accurately diagnosed after having developed. Often, at an early stage of said eye disease, the symptoms are initially attributed to astigmatism. Thus, it is only possible to accurately determine a keratoconus being at hand by means of an analysis of a corneal surface as well as of a corneal thickness or a posterior corneal surface. Currently, a possibility for early diagnosis of a keratoconus in the phase of development, without symptoms being obviously recognizable, is not known.

Regardless of the above-described keratometric method, it is generally known that, due to a cardiovascular activity of a living being or a person, an intraocular pressure of an eye of said person experiences a very small change. Corresponding to a pulse rate which is conditioned by a heart rate or to an alternating blood pressure change, an intraocular pressure of the eye is increased and reduced at substantially regular intervals. This is caused by the corresponding blood pressure increase inside the head, via which a force is applied on the eye. Said effect of the change in the intraocular pressure can, for instance, be measured with a so-called Pascal tonometer.

A Pascal tonometer comprises a tonometer head which has a concave shape, and which rests against a cornea, as well as an integrated electronic pressure sensor, with which an ocular pulse amplitude or a change in the intraocular pressure as a result of a cardiovascular activity can be measured. In this way, effects, conditioned by properties of the cornea as well as of the ocular pulse amplitude, on the measurement of the intraocular pressure can be eliminated, whereby the intraocular pressure can be measured very accurately. It is disadvantageous that this is an invasive measurement method. In the case of a measurement of the intraocular pressure with a non-contact tonometer, however, a measurement result is affected by the cardiovascular activity or an ocular pulse amplitude. Thus, a change in the intraocular pressure leads to a change in a topography of the cornea which is also very small. This disturbing effect of the cardiovascular activity which affects the measurement result of a tonometer measurement is not taken into account in the case of a measurement with a keratometer, since here, only a topography or radii of curvature are measured, and the very small change in the topography is not essential for the keratometer measurement.

SUMMARY OF THE INVENTION

The present invention is based on the task to provide a method and analysis apparatus for measuring a cornea, with which measuring a keratoconus at an early stage is possible.

With the method according to the invention for measuring a cornea of an eye to be examined of a living being, in particular of a person, with an ophthalmological analysis system, with the ophthalmological analysis system, a topography of a cornea is measured, wherein, with the ophthalmological analysis system, in a measurement time interval, a number of image data sets of a surface area of the cornea is obtained, wherein, in the measurement time interval, a change in an intraocular pressure of the eye is effected by a cardiovascular activity of the living being or of the person, wherein, due to said change in the intraocular pressure, a repeated change in the topography of the cornea in the measurement time interval is caused, wherein the repeated change in the topography of the cornea is determined by means of the ophthalmological analysis system from the number of image data sets, wherein a change in the topography of the cornea is measured, and wherein, in each case, the change is measured for points of the surface area of the cornea which were measured during the topography measurement.

As part of the method according to the invention, the otherwise undesirable effect of a repeated change in the topography of the cornea owing to the cardiovascular activity is utilized, in order to analyze the condition of the cornea more closely. Here, it is envisaged to obtain a number of image data sets of the surface area of the cornea within the measurement time interval. To this effect, the measurement time interval is at least long enough to enable determining a change in the topography of the cornea or measuring a period. Here, it is possible to measure a respective topography of the cornea for each image data set and, depending on the design of the ophthalmological analysis system, to carry out said measurement for a plurality of points on a corneal surface. Depending on the optical resolution of a respective recorded image of the corneal surface, the topography measurement can be carried out for up to each pixel of the respective image. By means of a comparison of coinciding points of the corneal surface from different image data sets, it is subsequently possible to measure the change or the movement in the examined surface area of the cornea in the measurement time interval.

By means of said measurement, conclusions on a changed geometry of the cornea can be drawn. In surface areas with, for instance, a reduced corneal thickness, in the area in question, in the case of an increase in the intraocular pressure as a consequence of the cardiovascular activity, there is an increased deflection or protrusion of the cornea of the change in the topography of the cornea which is conditioned by the increase in the intraocular pressure. In the area of reduced corneal thickness, the cornea can only summon up a low resistance against a pressure increase. Furthermore, areas of the corneal surface with deviating material properties, for instance with a reduced stiffness of the cornea, can also be measured in this way. As a whole, it is thus possible to locate surface areas of the cornea which have deviating properties from other surface areas by means of a non-invasive measurement of the cornea, whereby it is possible to draw conclusions on a potential disease of the areas of the cornea in question. In this way, diagnosing or determining a corneal disease which is at an early stage is substantially facilitated.

In particular, as part of the method, a probability of the development of a keratoconus can be derived from the measurement results of the respective changes in the points. Already before symptoms of an eccentric corneal steepening occur, it is possible to determine surface areas of the cornea which could develop a corneal steepening in the future due to, for instance, changed material properties. The ophthalmological analysis system can also comprise a database which contains data of conus stages of different persons. By means of a comparison of the measurement results with the stored measurement results of the persons, it is subsequently possible to calculate a probability of the development of a keratoconus. Furthermore, it is also possible to accurately recognize first symptoms of a keratoconus due to the measurement of the cornea, instead of, for instance, mistaking them for astigmatism.

Preferably, an amplitude of the change in the topography of the cornea can be measured, wherein then, in each case, the amplitude is measured for the points which were measured during the topography measurement. With a repeated change in the topography of the cornea, a maximum and/or minimum amplitude of the movement of a measured point can particularly easily be located. Therefore, the amplitudes in question are particularly well-suited as a reference for recognizing a cyclical repeated movement of the cornea. Furthermore, the amplitudes in question can be used as a standard for the movement of the cornea. Here, an amplitude is understood to be a maximum of a deflection of an alternating quantity. With the method according to the invention, at least an upper or maximum amplitude of the change in the topography of the cornea is determined, that is the amplitude which is conditioned by a systolic cardiovascular activity. In consequence, the amplitude which is caused by a diastolic cardiovascular activity is here understood to be a lower or minimum amplitude.

In one embodiment of the method, a comparison of average values of the respective repeated changes in the points can be carried out. In this way, the measurement time interval can be selected such that a plurality of repeated changes in the topography of the cornea can be measured. In particular by means of the measurement of the plurality of repeated changes, the measurement accuracy can be further improved, since then, repeatedly occurring changes in the surface area can be accurately determined. In this way, it is possible to measure a period duration of the change in the topography of the cornea, wherein, for the respective measurement of the period duration, for instance a maximum amplitude, a minimum amplitude, a root-mean-square value or an actual value of the respective amplitude or period duration can be determined. For instance, the average values for the measured points of the surface area can then be measured under a maximum intraocular or systolic pressure, in order to locate areas of the surface area of the cornea in which the averages values significantly deviate from average values of comparable points and areas of the cornea, respectively. Alternatively, it is also possible to calculate the values in question starting from, for instance, a minimum amplitude of the change in the topography of the cornea.

In another embodiment of the method, a comparison of the measured change in the topography of the cornea in relation to a presumed change in the topography of the cornea for the respective points can be carried out. This can be effected in that, for instance, the measured maximum amplitude for a point of the surface area of the cornea is compared to a value for a presumed amplitude. This can be carried out for all measured points of the surface area of the cornea. The presumed values for the respective points can, for instance, be taken from a database of the ophthalmological analysis system. The comparison can be carried separately or also in combination with calculating an average value of the repeated changes in the points.

Furthermore, with a second analysis system, for instance a cardiological one, a cardiovascular activity of a person to be examined can be measured, wherein then, with the second analysis system, a number of measurement data sets of a cardiovascular rate of the person in the measurement time interval can be obtained, wherein the repeated change in the topography of the cornea from the number of image data sets can be synchronized with the measurement data of the cardiovascular rate in the measurement time interval. The cardiovascular activity can be determined by means of a number of measurement methods. Parallel to the measurement of the change in the topography of the cornea, in the same measurement time interval, the cardiovascular rate of the person to be examined can be measured and a number of measurement data sets can be obtained in the measurement time interval and be recorded. The measurement data sets can be synchronized with the image data sets of the ophthalmological analysis system by means of a processing unit for data processing. Here, an adaptation of the measurement data sets to the image data sets, or vice versa, can be effected. The synchronization can be carried out in such a manner that a change or an amplitude and a period, respectively, of the cardiovascular activity substantially corresponds to a change or an amplitude and a period, respectively, of the change in the topography of the cornea. This is particularly easily possible since the change in the topography of the cornea is caused by or depends on the cardiovascular activity. The synchronization has the advantage that the change or the amplitude of the change in the topography of the cornea can particularly accurately be determined and potential other factors which can cause a change in the topography of the cornea, such as a tear film, blinking, or a changed fixation of the eye, can be excluded or filtered out. In a measurement time interval comprising multiple periods, the respective changes or amplitudes of the change in the topography of the cornea, which are conditioned the cardiovascular activity, can then particularly accurately be determined.

Furthermore, it is then also possible to correct a phase of the change in the topography relative to a phase of the cardiovascular rate. This can be effected, for instance, in relation to an absolute height of an amplitude or of a rate and a period, respectively. Potential changes in a cardiovascular activity during the measurement time interval can thus be taken into account when interpreting the change in the topography of the cornea. In this way, potential measurement errors can still be further minimized. For instance, a measurement time interval can have a duration of up to one minute.

Advantageously, the second analysis system can be a sphygmologic analysis system. A sphygmologic analysis system for measuring a pulse can be procured particularly easily and at low costs and can easily be combined with an ophthalmological analysis system, for instance in a common housing. In a particularly easy version, a pulse measurement can be effected on a finger or an ear of a person to be examined. Here, the person is hardly affected at all by the pulse measurement. Alternatively, it is, as a matter of course, also possible to measure the cardiovascular activity by means of another known method, such as an electrocardiogram.

It is particularly advantageous if the systolic arterial pulse is measured. Said pulse offers information on, amongst other things, an absolute pressure of the vessels and is thus particularly suitable for a synchronization with a maximum amplitude of the topography measurement. Alternatively, it is, as a matter of course, also possible to measure the diastolic pulse.

It can also be envisaged to continuously measure a blood pressure change. In this case, it is possible to continuously monitor a pulse and the blood pressure change, respectively, whereby determining the systolic and/or diastolic pulse becomes possible in a particularly easy manner. Particular repeated time intervals of the blood pressure change can then also be used for a measurement or for the synchronization of the repeated change in the topography of the cornea. Furthermore, the continuous measurement of the blood pressure change can also be stored for an evaluation at a later stage.

Furthermore, the change in the topography between a beginning and an end of the systole can be measured. With respect to a blood pressure change, this means that in the range of an increase of the blood pressure, that is on an end of the diastole or a beginning of the systole, and of a maximum amplitude or in the range of a maximum value of the blood pressure of the systole in question, that is on an end of the systole or a beginning of the diastole, a change in the topography in the respective points of the cornea can be measured. By relating the measurement to the previously mentioned portion of the systole, it is then possible to measure a change in the movement of the topography during the period of time in question, between the beginning and the end of the systole. The change in the movement can, for instance, be illustrated in a path-time diagram, wherein, for the change in the topography between the beginning and the end of the systole, a gradient of a curve of the change in the movement can be determined in each case.

Even more accurate measurement results can be achieved if the change in the topography is measured between a minimum pulse amplitude and a maximum pulse amplitude. Said pulse amplitudes can comparatively reliably be determined.

From the change in the topography of the cornea, furthermore, a change in the curvature $\Delta C$ of the cornea can be derived. A change in the curvature can in particular result from the fact that an intraocular pressure is increased, as previously described, by the cardiovascular activity. Thus, not only a relative movement of a point of the surface of the cornea can be measured in this case, but it can also be determined at the same time which changes in the curvature $\Delta C$ of the cornea result from the movement of the point. For this, it is then required to simultaneously measure a multiplicity of points of the surface of the cornea.

Optionally, a relative movement of the surface area of the cornea in the direction of a longitudinal axis of the examined eye of at least 0.01 mm can be measured. With this measurement accuracy, it becomes already possible to carry out the method for measuring the cornea. This measurement accuracy can, for instance, be achieved if a keratometer is used as the ophthalmological analysis apparatus.

Advantageously, by means of the measurement time interval, an average value can be calculated for the respective changes in the curvature $\Delta C$ of the points. If the change in the topography of the cornea was not synchronized with the cardiovascular activity, the average value would be zero over a long measurement time interval, since, in that case, almost all portions of a curve of a movement of a point would be taken into account in a path-time diagram here. By means of a synchronization with the cardiovascular activity or a blood pressure change, respectively, and a measurement of the change in the curvature $\Delta C$ in portions which are defined by the blood pressure change, for instance an increase area of a systole in each case, calculating an average value of a change in the curvature $\Delta C$ then always leads to a positive value. Said values are then also comparable for the measured points of the surface area of the cornea, in such a way that surface areas of the cornea can present a higher or a lower average value of a change in the curvature $\Delta C$. From such measurement results, particularly reliable indications on a condition of a corneal material can then be derived.

A stiffness of the cornea for the measured points of the surface area of the cornea in each case can be determined as a material property of the cornea, which can be used for determining a keratoconus, wherein the stiffness of the cornea can be derived from an increase in the change in the curvature $\Delta C$. Thus, a distribution of the stiffness of the cornea over the measured surface area can be obtained as a measurement result, whereby it is again possible to draw conclusions on a disease of the cornea and of the eye, respectively. For instance, a particularly dramatic change in the curvature $\Delta C$ in a corneal area compared to otherwise small changes in the curvature $\Delta C$ in the rest of the corneal areas allows the conclusion that the corneal area with the dramatic or large change in the curvature is particularly flexible and thus less stiff. The resistance of the corneal material against a deformation by a force is here understood to be stiffness. The stiffness of the cornea depends on the elasticity of the corneal material or of the elasticity module or of the thrust module, but also on the size and shape of the cross-sectional surface of the cornea in question.

A person to be examined is particularly little affected during the measurement of the cornea if a non-invasive measurement of the cardiovascular rate is carried out. A measurement of a pulse on a finger or an ear substantially corresponds to a non-invasive measurement. Basically, by means of the non-invasive measurement of the cardiovascular rate, the goal of measuring an ocular pulse cycle is pursued. This can also be effected by means of an invasive measurement directly on the eye to be examined, but the patients or persons in question perceive this as unpleasant.

Furthermore, with the ophthalmological analysis system, a measurement of a tear film can be carried out from the image data sets in the measurement time interval. If the measurement time interval is selected long enough to change the existing tear film in the surface area of the cornea which is recorded with the ophthalmological analysis system, and that, for instance, the tear film breaks up, the topography measurement of the surface area can be distorted, amongst other things. Indeed, a change in the tear film is effected in comparison to a cardiovascular activity and is thus relatively slow compared to a change in the topography of the cornea depending thereupon, and can thus easily be recognized. Furthermore, a change in the topography of the cornea which is conditioned by a cardiovascular activity is smaller than a change in the topography which is conditioned by a change in the tear film. Therefore, the change or the amplitude of the change in the topography of the cornea can easily be corrected corresponding to the measurement data of the tear film or of a change in the tear film. In this way, the measurement of the cornea can be carried out even more accurately.

For the purpose of an improved demonstration and evaluation by an operator, the measurement results of the changes in the points can graphically be illustrated as a map of a corneal surface. The graphical illustration can, for instance, comprise isolines or a color gradient illustration for marking the isolines. Furthermore, perspective illustrations as well as illustrations of deviations in a surface area of an eye are possible. The illustration of the measurement results can be effected by means of the ophthalmological analysis system, such that, immediately after a measurement of a cornea, a measurement result is directly available to an operator.

The ophthalmological analysis apparatus according to the invention for measuring a cornea of an eye to be examined, in particular of a person, comprises an ophthalmological analysis system, wherein the ophthalmological analysis system serves to measure a topography of a cornea, wherein the ophthalmological analysis system is formed such that, in a measurement time interval, a number of image data sets of a surface area of the cornea can be obtained, wherein subsequently, in the measurement time interval, a change in an intraocular pressure of the eye is effected by a cardiovascular activity, and due to said change in the intraocular pressure, a repeated change in the topography of the cornea in the measurement time interval is caused, wherein the ophthalmological analysis system comprises a processing unit, by means of which the repeated change in the topography of the cornea can be determined from the number of image data sets, wherein, by means of the processing unit, a change in the topography of the cornea can be measured, and wherein, in each case, the change can be measured for points of the surface area of the cornea which were measured during the topography measurement.

Concerning the advantageous effects of the ophthalmological analysis apparatus, reference is made to the description of the method according to the invention.

Advantageously, the ophthalmological analysis apparatus can be a keratometer. With a keratometer, a topography of a cornea can particularly easily be measured and determined.

Further possible embodiments of the ophthalmological analysis apparatus result from the descriptions of the features disclosed herein.

BRIEF DESCRIPTION OF THE DRAWINGS

In the following, a preferred embodiment of the invention is explained in more detail with reference to the enclosed drawings.

In the drawings.

DETAILED DESCRIPTION OF THE EXAMPLE EMBODIMENTS

Figure 1:
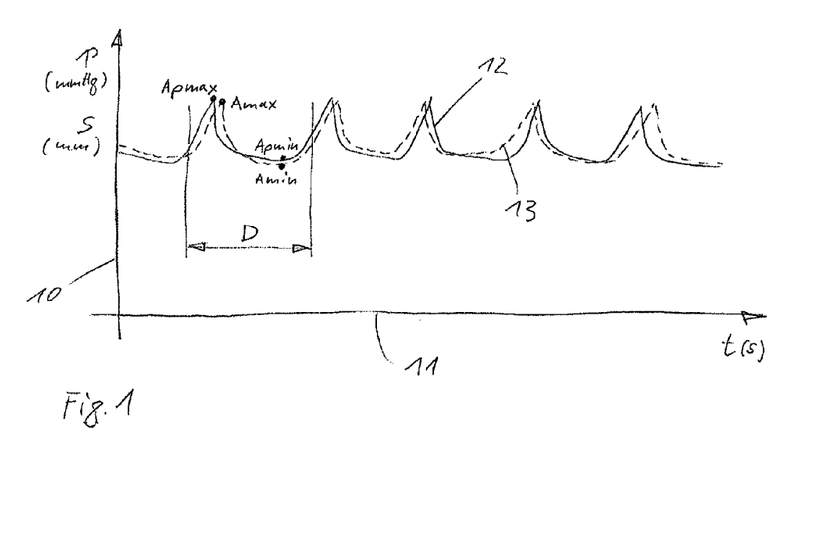
FIG. 1 shows a diagram illustration of a cardiovascular activity and of a change in the movement of a point of a cornea.

FIG. 1 shows a diagram illustration of a change in a cardiovascular activity or in a pulse of a person. On an axis of ordinates 10, a pressure in mmHg and on an axis of abscissas 11, a time in seconds of a repeated change in the pulse is illustrated in the form of a waveform continuous line 12. Furthermore, on the axis of ordinates 10, a path S in mm is illustrated for a waveform dashed line 13. Here, the illustrated time interval corresponds to a measurement time interval of a measurement. The path S is related to a point P on a surface 14 of a cornea 15, wherein the line 13 illustrates a displacement or a movement of the point P in the direction of an optical axis 16 of an eye 17. Here, for the purpose of an improved demonstration, the line 13 corresponds an illustration, which is substantially idealized, of a movement without factors which distort the movement, such as a change in the tear film, blinking or a change in the fixation or an eye movement.

Figure 2:
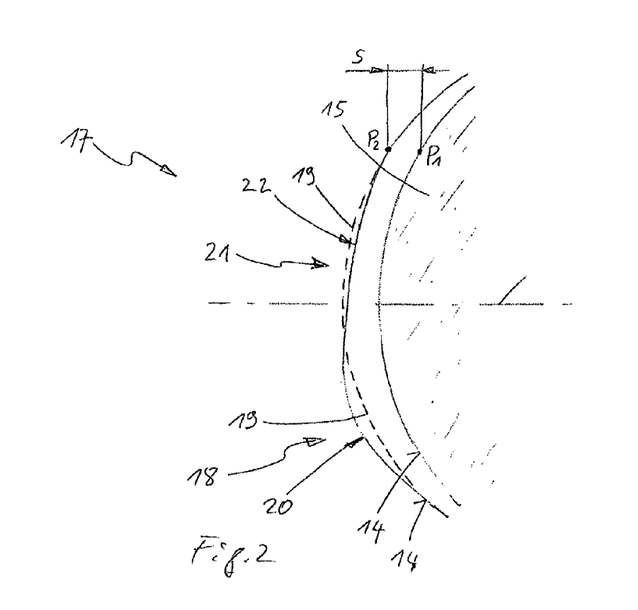
FIG. 2 shows a schematic sectional view of the cornea of an eye.
Figure 6:
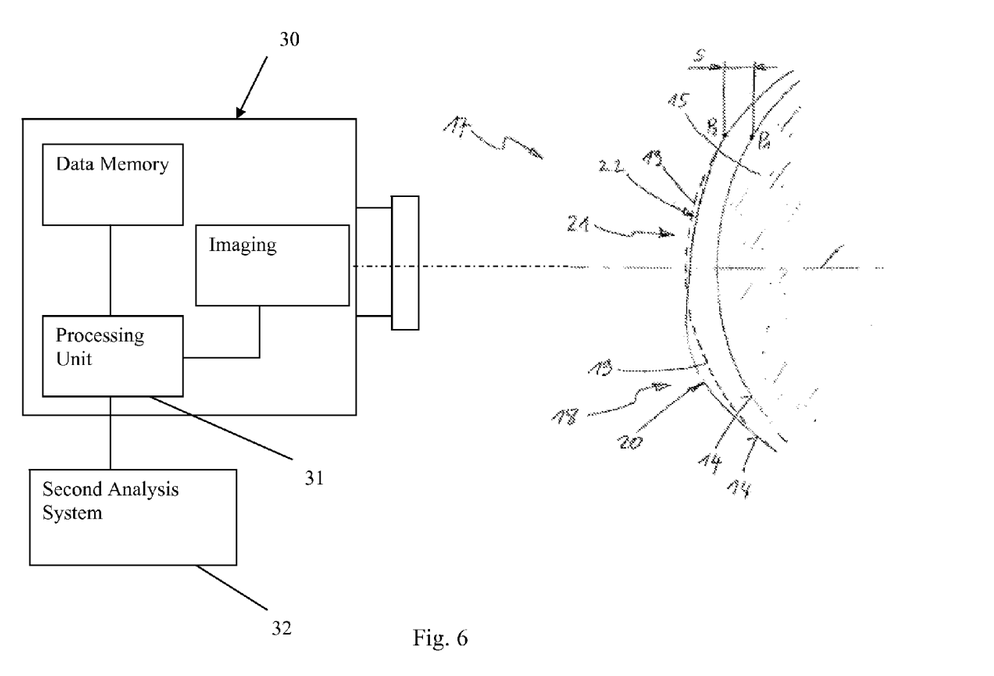
FIG. 6 shows a block diagram of an ophthalmological analysis system for measuring and processing data corresponding to the cornea of an eye.

As shown in FIG. 2, by means of an increase of an intraocular pressure of the eye 17, which is only partially illustrated here, the surface 14 of the cornea 15 is moved substantially in the direction of the optical axis 16 in such a way that the point P moves from a position P1 by path S to a position P2. Said movement of the point P as well as a movement of other points which are not designated in more detail here, and which describe the surface 14 of the cornea is measured during the measurement time interval by means of a keratometer, which is also not illustrated in more detail here, in that a number of image data sets is recorded. In this way, it becomes possible to measure a change in a topography of the cornea 15 for a plurality of points P. An ophthalmological system 30 which can include, for example, a keratometer, as described above, can be used to record images, store databases of image data, and analyze the data using a processing unit 31 as shown in FIG. 6. The processing unit 31 is in communication with a second analysis system 32 which can include, as described herein, a cardiological, sphygmologic, or similar system.

As can be taken from a period duration D of the repeated change in the point P of the topography by way of example, the point P, in position P1, is on a minimum amplitude Amin, and in position P2, on a maximum amplitude Amax of the line 13. Here, the line 13, which illustrates the deflection of the point P relative to the measurement time interval, is synchronized with line 12, which illustrates a pulse or a blood pressure change relative to the measurement time interval. Therefore, with a maximum amplitude Apmax and a minimum amplitude Apmin of a pulse, the line 12 attains overlapping with the line 13 to the greatest possible extent.

In FIG. 2, furthermore, a surface area 18 of the cornea 15 is illustrated which, during a maximum deflection of the cornea 15 compared to a presumed deflection, which is illustrated with a dashed line 19 here, is protruded in the surface area 18 or has an eccentric corneal steepening relative to the optical axis 16. Said protrusion 20 is conditioned by a weakening of a corneal tissue in the surface area 18 and is a first significant sign for the development of a keratoconus in the surface area 18. Furthermore, due to the protrusion 20, the cornea 15 is flattened in a surface area 21 or forms a flat portion 22 relative to the presumed deflection or line 19.

Figure 3:
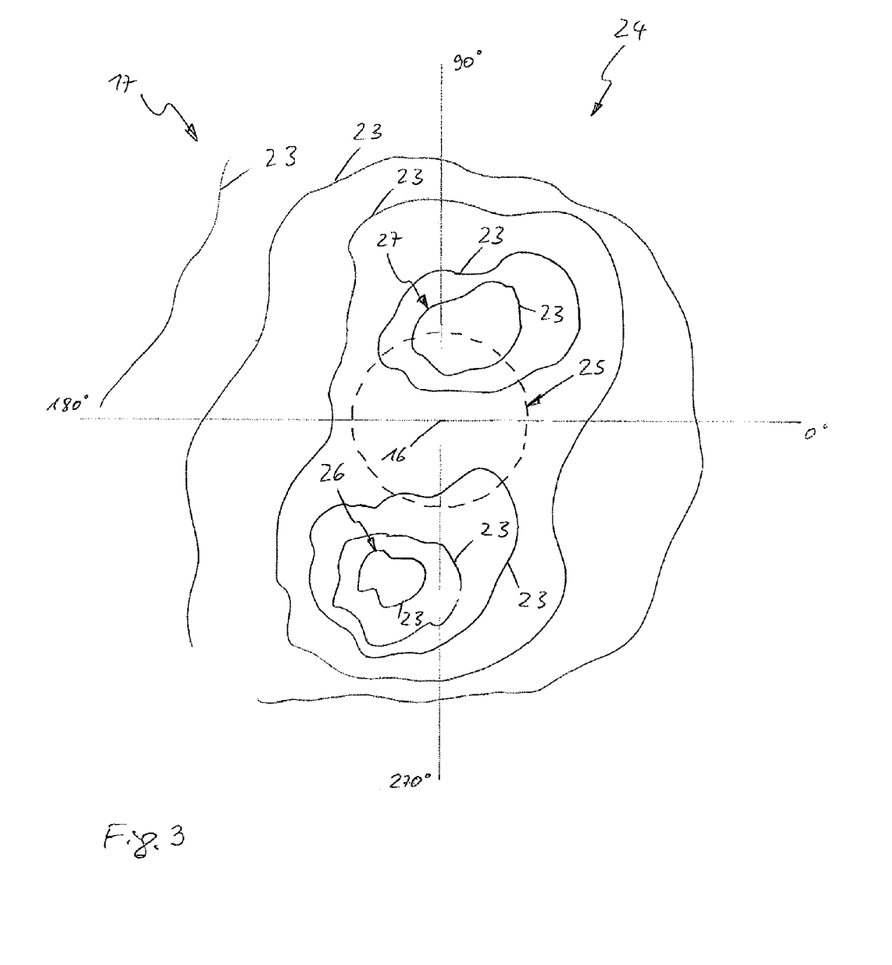
FIG. 3 shows a diagram illustration of a surface area of a cornea.

FIG. 3 shows a diagram illustration of the cornea 15 with isolines 23 which respectively illustrate different quantities of an average value for the respective measured points of the cornea 15. The diagram illustration comprises a substantially entire surface area 24 of the cornea 15 which corresponds to a measurement area of the keratometer. Coaxially to the optical axis 16, the pupil 25 is indicated. From the different average values of the respective amplitudes of the change in the topography of the cornea 15, which are illustrated by means of the isolines 23, it can be taken from the exemplary illustration which is shown here that, in a surface area 26, comparatively high average values are measured. These average values are conditioned by a stronger deflection of the cornea 15 in the surface area 24, whereby it is possible to conclude that a keratoconus is developing. Furthermore, in a surface area 27, analogously to the example according to FIG. 2, a reduced deflection of the cornea 15 results, which is reflected in comparatively low average values. From this, it can be concluded that there is a flat portion in the surface area 27.

Figure 4:
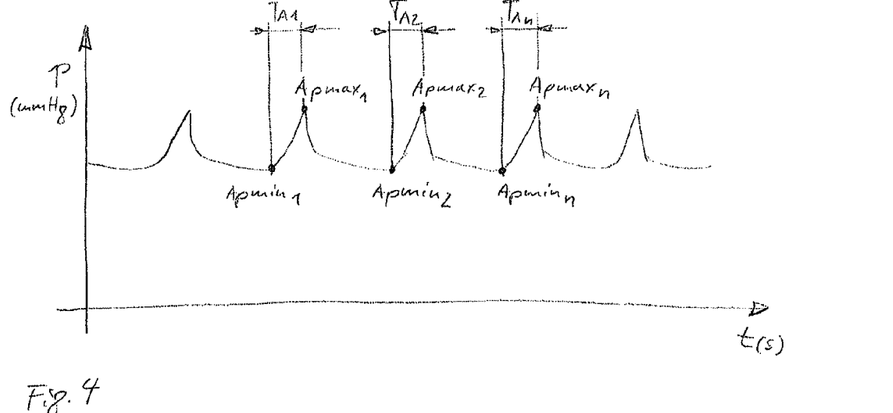
FIG. 4 shows another diagram illustration of a cardiovascular activity.
Figure 5:
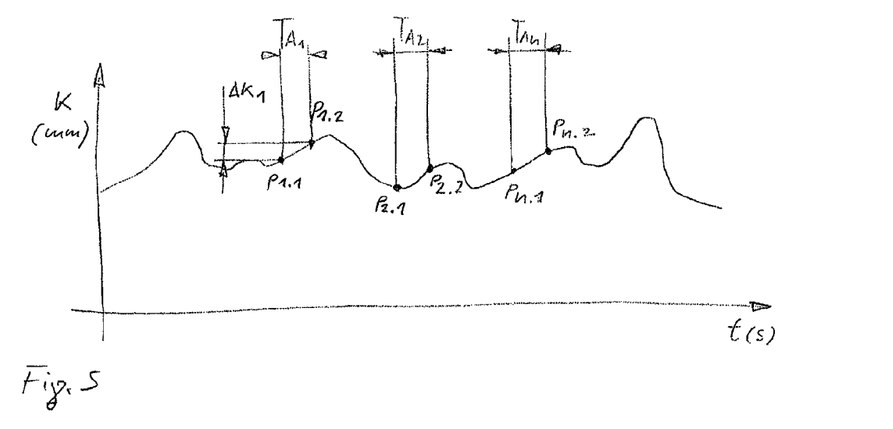
FIG. 5 shows another diagram illustration of a change in the movement of a point of a cornea.

A simultaneous view of the FIGS. 4 and 5 shows, as already shown in FIG. 1, diagram illustrations of a change in a cardiovascular activity or a change in the curvature $\Delta C$. According to FIG. 4, a continuous blood pressure measurement is effected, wherein here, the maximum and the minimum amplitudes or the points of the beginning and the end of a systole are determined in each case. After a synchronization with a change in the topography of the cornea, a measurement of a change in the curvature $\Delta C$ in the coinciding time interval TA in question is effected. The diagram in FIG. 5 shows a shifting change in the curvature $\Delta C$ with respect to the illustrated measurement time interval, with which the change in the curvature does not proceed ideally, but is subject to further factors, for instance a change in a tear film, due to blinking, or a change in a fixation of the eye. Therefore, for the point Apmin1 in the diagram of the cardiovascular activity, the change in the curvature in the point P1.1 in the diagram of the change in the curvature is determined at the same time and subsequently, for the point Apmax1, the change in the curvature in the point P1.2. From this, an increase in the change in the curvature between the point P1.1 and the point P1.2 can be determined. Said increase in the change in the curvature is determined for the respective time intervals TA1, TA2 to TAn and an average value of the change in the curvature is calculated. The average value of the change in the curvature thus forms a comparable measure for all measured points P of the surface area of the cornea. Thus, it becomes in particular possible to analyze in detail the change in the topography of the cornea or in the point P which is illustrated here, which is conditioned by the cardiovascular activity or by other factors, and, if required, to filter out changes which overlap said change and which are caused by other factors.

The invention claimed is:

1. A method for non-invasively evaluating a cornea of an eye to evaluate a keratoconus disease state, said method comprising:
    measuring a cardiovascular activity of a person using a cardiovascular analysis system and acquiring a number of measurement data sets of a cardiovascular rate in a measurement time interval;
    measuring a topography of a cornea and obtaining a number of image data sets of a surface area of the cornea using an ophthalmological analysis system during the measurement time interval when the intraocular pressure of the eye is changing due to the cardiovascular activity;
    identifying a repetitive change in the topography of the cornea from the number of image data sets, wherein, in each case, the change is measured for points (P) of the surface area of the cornea; and
    deriving a probability of development of a keratoconus from the repeated change in the topography of the cornea from the acquired data;
    wherein the repeated change in the topography of the cornea is synchronized with the measurement data of the cardiovascular rate in the measurement time interval.

2. The method according to claim 1 in which an amplitude of the change in the topography of the cornea is measured, wherein, in each case, the amplitude is measured for the points (P) which were measured during the topography measurement.

3. The method according to claim 1 in which a comparison of average values of the respective repeated changes in the points (P) is carried out.

4. The method according to claim 1 in which a comparison of the measured change in the topography of the cornea in relation to a presumed change in the topography of the cornea for the respective points (P) is carried out.

5. The method according to claim 1, in which a phase of the change in the topography is corrected relative to a phase of the change in the cardiovascular rate.

6. The method according to claim 1, in which the cardiovascular analysis system is a sphygmologic analysis system.

7. The method according to claim 1, in which the systolic arterial pulse is measured.

8. The method according to claim 1, in which a blood pressure change is continuously measured.

9. The method according to claim 1, in which the change in the topography is measured between a beginning and an end of the systole.

10. The method according to claim 1, in which the change in the topography is measured between a minimum pulse amplitude and a maximum pulse amplitude.

11. The method according to claim 9 in which from the change in the topography of the cornea, a change in the curvature ($\Delta C$) of the cornea is derived.

12. The method according to claim 11, in which using the measurement time interval, an average value is calculated for the respective changes in the curvature ($\Delta C$) of the points (P).

13. The method according to claim 11 in which an increase in the change in the curvature ($\Delta C$) is derived, wherein, from the increase, a stiffness of the cornea is, in each case, determined for the measured points (P) of the surface area of the cornea.

14. The method according to claim 1, in which a non-invasive measurement of the cardiovascular rate is carried out.

15. The method according to claim 1, in which with the ophthalmological analysis system, a measurement of a tear film is carried out from the image data sets in the measurement time interval, wherein the change in the topography is corrected corresponding to the measurement data of the tear film.

16. The method according to claim 1, in which the measurement results of the changes in the points (P) are graphically illustrated as a map of a corneal surface.

17. An ophthalmological analysis apparatus for measuring a cornea of an eye to determine a probability of developing keratoconus, said apparatus comprising:

an ophthalmological analysis system measuring a topography of a cornea experiencing a change in intraocular pressure due to cardiovascular activity as measured by a cardiovascular analysis system in a measurement time interval, and obtaining a number of image data sets of a surface area of the cornea; and a processing unit identifying a cyclical change in the topography of the cornea from the number of image data sets, wherein the processing unit identifies a change in the topography of the cornea by evaluating a change in points (P) of the surface area of the cornea during the change in intraocular pressure caused by cardiovascular activity, synchronizes the change in the topography of the cornea with the cardiovascular activity in the measurement time interval, and derives a probability of development of a keratoconus from a comparison of the cyclical change in the topography of the cornea identified from the number of image data sets to a database containing data of conus stages.

18. The analysis apparatus according to claim 17, in which the ophthalmological analysis apparatus is a keratometer.

* * * * *